US012623084B2

(12) United States Patent
Josi et al.

(10) Patent No.:    US 12,623,084 B2
(45) Date of Patent:        May 12, 2026

(54) INSERTION TOOL FOR POUCHES FOR IPGs

(71) Applicant: Hylomorph AG, Zürich (CH)

(72) Inventors: Benjamin Josi, Bülach (CH);
Francesco Robotti, Zürich (CH);
Simone Bottan, Zürich (CH); **Aldo
Ferrari**, Zürich (CH)

(73) Assignee: Hylomorph AG, Zürich (CH)

( * ) Notice: Subject to any disclaimer, the term of this
patent is extended or adjusted under 35
U.S.C. 154(b) by 508 days.

(21) Appl. No.: 18/008,024

(22) PCT Filed: May 25, 2021

(86) PCT No.: PCT/EP2021/063880
§ 371 (c)(1),
(2) Date: Dec. 2, 2022

(87) PCT Pub. No.: WO2021/244901
PCT Pub. Date: Dec. 9, 2021

(65) Prior Publication Data
US 2023/0256255 A1      Aug. 17, 2023

(30) Foreign Application Priority Data
Jun. 5, 2020    (EP) .................................... 20178539

(51) Int. Cl.
A61N 1/375          (2006.01)
A61N 1/372          (2006.01)
(52) U.S. Cl.
CPC ....... A61N 1/37518 (2017.08); A61N 1/3752
(2013.01)

(58) Field of Classification Search
CPC .. A61N 1/37518; A61N 1/3752; A61N 1/372;
A61N 1/375
See application file for complete search history.

(56) References Cited

U.S. PATENT DOCUMENTS

2005/0267543 A1    12/2005  Heruth et al.
2006/0253181 A1*   11/2006  Schulman ............ A61N 1/0551
                                                                            607/116

(Continued)

FOREIGN PATENT DOCUMENTS

CN          109 125 924  A      1/2019
KR              200341492  Y1 *   2/2004
WO          2019/113451  A1      6/2019

OTHER PUBLICATIONS

English Translation of KR-200341492-Y1 (Year: 2004).*

(Continued)

*Primary Examiner* — Brian T Gedeon
(74) *Attorney, Agent, or Firm* — Sughrue Mion, PLLC

(57)                    ABSTRACT

An insertion tool having a wall of tubular or funneled shape,
with, on a front portion thereof, a front side opening so that
an opening of an empty pouch for an implantable pulse
generator, and corresponding wiring, can be shifted onto the
front portion and over the front side opening, and with, on
a back portion of the insertion tool, a backside opening so
that an implantable pulse generator, and corresponding
wiring, can be inserted through that backside opening,
through a passageway opening to the front side opening and
into the pouch, while manually holding the insertion tool
using the back portion The wall has an axial slot between the
front side opening and the backside opening.

34 Claims, 7 Drawing Sheets

(56)     References Cited

U.S. PATENT DOCUMENTS

| | | |
|---|---|---|
| 2012/0059467 A1 | 3/2012 | Drew et al. |
| 2015/0238262 A1 | 8/2015 | Buevich et al. |
| 2019/0117836 A1 | 4/2019 | Matheny |
| 2019/0262510 A1 | 8/2019 | Chen et al. |
| 2019/0351241 A1 | 11/2019 | Novak |

OTHER PUBLICATIONS

International Search Report for PCT/EP2021/063880 dated Aug. 4, 2021.
Written Opinion for PCT/EP2021/063880 dated Aug. 4, 2021.

* cited by examiner a)

b)

c)

d)

a)

b)

c)

d)

a)

b)

c)

d)

INSERTION TOOL FOR POUCHES FOR IPGs

CROSS REFERENCE TO RELATED APPLICATIONS

This application is a National Stage of International Application No. PCT/EP2021/063880 filed May 25, 2021, claiming priority based on European Patent Application No. 20 178 539.1 filed Jun. 5, 2020.

TECHNICAL FIELD

The present invention relates to insertion tool with which implantable pulse generators can be inserted into correspondingly adapted pouches or envelopes or sleeves prior to implantation, to uses of such insertion tools, as well as to methods how to insert implantable pulse generators into pouches, envelopes or sleeves using such insertion tools.

PRIOR ART

Implantable Pulse Generators (IPGs) provide electrical stimulation and are integral parts of devices such as pacemakers, implantable cardioverter defibrillators, or neurostimulators. IPGs remain implanted for several years before either being exchanged due to battery depletion, or upgrade to device providing additional functionality. Examples of medical devices incorporating implantable pulse generators are Cardiac Implantable Electronic Devices (CIEDs) such as pacemakers, implantable cardioverter defibrillators, and devices for cardiac resynchronization therapy, but also implantable neurostimulators such as vagus nerve stimulators, spinal cord neuromodulators, deep brain stimulators, sacral nerve stimulators, etc.

These implantable electronic devices exert their function upon deployment in the body, generally in contact with soft tissue. The implantation procedure requires the generation of a surgical pocket (i.e. a space in the tissue) to provide room to the implant. Despite the high level of development of these implants, some significant risks remain associated with their implantation, because the devices comprise synthetic materials at their interface with the surrounding tissue. The risks are related to complications mostly arising at the level of the surgical pocket, due to local infection and/or to the body fibrotic response to artificial materials. Altogether, these adverse events can cause pain and discomfort, but also more serious threats to the patient's life, leading in the worst cases to revision surgeries with additional costs and risks.

To tackle these problems a number of solutions in the form of specific medical devices have been recently proposed for the management of surgical pocket health. These medical devices have generally the form of protective pouches, envelopes or sleeves, into which the casing and the proximal part of the leads of the implanted device (the CIED or neurostimulator) are inserted before deployment in the surgical pocket. The pouches can have purely stabilization purposes (i.e. to support the regeneration of the tissue surrounding the implant in the surgical pocket), or may also provide additional functions such as the delivery of active molecules (e.g. antibiotics) or the enforcement or stimulation of an antifibrotic barrier.

US 2012059467 discloses a cover for receiving an implantable medical device with self-anchoring protrusions that engage tissue of a pocket where the device is implanted to resist movement including rotation and flipping. The implantable medical device is placed into the cover prior to being placed into the pocket so that once in the pocket, the device may reduce rotating, flipping, or otherwise moving. The self-anchoring protrusions may include barbs of various shapes to frictionally engage the tissue of the pocket. The cover may include features such as a strap and elastic construction to assist in holding the implantable medical device within the cover. Apertures may be included to enable the device. The cover may include additional features like suture tabs to allow additional fixation via suturing the cover to the surrounding tissue.

WO 2019/113451 discloses a resorbable bioelectric device with multiple first reservoirs and multiple second reservoirs joined with a planar substrate. Selected ones of the multiple first reservoirs include a reducing agent, and first reservoir surfaces of selected ones of the multiple first reservoirs are proximate to a first substrate surface. Selected ones of the multiple second reservoirs include an oxidizing agent, and second reservoir surfaces of selected ones of the multiple second reservoirs are proximate to the first substrate surface. US 2005/267543 discloses an anti-infective covering for an implantable medical device which may be a polymeric boot that comprises an anti-infective agent in an amount effective to prevent an infection when implanted in a pocket of a patient. The boot is configured to snuggly engage at least a portion of the implantable medical device. The boot may contain a side hole that allows a housing of the implantable medical device to serve as a return electrode. The boot may be placed about the implantable medical device to render the device anti-infective.

US 2019/351241 describes implantable pouch products having a segmental lamination structure that provides an interior pocket for receiving a medical device, for example an electronic medical device such as a cardiac pacemaker or defibrillator. Also described are methods for making and using such products.

US 2019/117836 discloses an implantable medical product and method of use for substantially reducing or eliminating harsh biological responses associated with conventionally implanted medical devices, including inflammation, infection and thrombogenesis, when implanted in in a body of a warm blooded mammal. The bioremodelable pouch structure is configured and sized to receive, encase and retain an electrical medical device therein and to allow such device to be inserted into the internal region or cavity of the pouch structure; with the pouch structure formed from either: (a) first and second sheets, or (b) a single sheet having first and second sheet portions. After receiving the electrical device, the edges around the opening are closed by suturing or stapling. The medical device encased by the bioremodelable pouch structure effectively improves biological functions by promoting tissue regeneration, modulated healing of adjacent tissue or growth of new tissue when implanted in the body of the mammal.

US 2015/238262 relates to a biodegradable and resorbable polymer pouch for use with cardiac rhythm management devices (CRMs) and other implantable medical devices (IMDs), i.e., a pouch, covering, or other receptacle capable of encasing, surrounding and/or holding the CRM or other IMD for the purpose of securing it in position, inhibiting or reducing bacterial growth, providing pain relief and/or inhibiting scarring or fibrosis on or around the CRM or other IMD. Optionally, the biodegradable and resorbable pouches include one or more drugs in the polymer matrix to provide prophylactic effects and alleviate side effects or complications associated with the surgery or implantation of the CRM or other IMD.

US 2019/262510 proposes a kit including a mesh substrate and a polymer that is fixed to the mesh substrate. The polymer includes an active agent that is configured to elute over time. The kit further includes a hemostatic agent. The hemostatic agent is separate from the mesh substrate and the polymer. Systems and methods are disclosed.

CN 109 125 924 discloses an application of a biological sleeve in cardiac implantation of an electronic instrument, which is used for inserting a pulse generator of a cardiac implantable electronic instrument such as a cardiac pacemaker and a defibrillator, and then implanting the pulse generator into a capsule formed by subcutaneous tissue together. As the biological sleeve is an acellular matrix, the biological sleeve has good biocompatibility, certain mechanical property, biodegradability, antibacterial ability and the like, and can reduce the incidence of complications such as capsule infection, hematoma, ulceration and the like after cardiac implantation of electronic instruments.

SUMMARY OF THE INVENTION

Typically, such pouches (including envelopes or sleeves) for implantable electronic devices comprise or consist of soft and thin material, which is challenging to handle. For example, if the pouch is an implantable seamless pouch manufactured from pure biosynthesized cellulose which provides long-term protection of the surgical pocket tissue from fibrotic tissue build up associated with the foreign body reaction against implantable pulse generators. A pouch is a small flexible bag in the form of a preferably essentially tubular pocket which is typically closed at a bottom end and which has an opening at the top end for inserting the IPG device, It can be made of one single material or from a multilayer material, and it can be single-piece or multi-piece.

The process of insertion of the target device into the pouch is performed immediately before the deployment of the implant (the pouch containing the target device) into the surgical pocket, in the operating room and under aseptic conditions. The insertion is therefore a delicate step that requires a timely procedure with minimal risk of contamination or damage of the implant or of the pouch. Currently, this procedure is performed purely manually by the surgeon without any aid.

The invention at hand provides a dedicated tool in the form of an insertion tool to standardize, speed up, and avoid contamination/damage during the insertion of a target device into a protective pouch. The proposed tool can be a single body or multicomponent tool.

The tool is a surgical applicator/loading tool. It is designed to simplify and speed up the process of introducing a Cardiovascular Implantable Electronic Device (CIED) and/or Neurostimulators into a pouch/envelope.

The main functions of the applicator are to facilitate the process during all steps of the insertion, in particular:

finding the opening of the pouch
    inserting the applicator in the pouch
    spreading the pouch open/preparing the pouch to the loading of the Device including the proximal leads
    holding the pouch open and providing access to the Device and electrodes
    provide access to the cellulose pouch while minimizing the distance between the pouch and the body
    provide access to the cellulose pouch with a structure that guides/constrains the part of the leads that is coiled up behind/around the Device generator
    provide access to multiple implants/sizes through a parametric design model.

The present invention in line with this proposes an insertion tool having a wall of essentially tubular or preferably funneled shape (converging to the front opening), and having, on a front portion thereof, a front side opening suitable and adapted so that an opening of an empty pouch for an implantable pulse generator, and, if present, corresponding wiring/electrodes, can at least partially be shifted onto said front portion and over said front side opening.

Furthermore the insertion tool has, on a back portion of the insertion tool, a backside opening suitable and adapted so that an implantable pulse generator, and, if present, corresponding wiring/electrodes, can be inserted through that backside opening, through a passageway opening to the front side opening and into said pouch, while manually holding the insertion tool using said back portion. Preferably, according to the invention said wall comprises an axial slot between the front side opening and the backside opening (the axial direction being defined as the direction along the passageway between the backside opening in the front side opening).

The insertion tool provides a surprisingly simple but very efficient help for the delicate task to put an implantable pulse generator, and if present, corresponding wiring, into such a pouch, under aseptic conditions with as little contact with the pouch and the device, and without any risk of damage to the pouch. Such pouches are made of thin, often slippery and challenging to handle material, and the tool effectively provides an essential help for inserting the device into such a pouch.

According to a first preferred embodiment, at said front side opening there is provided a latch axially protruding beyond a front edge of the front side opening. Preferably such a latch is provided with rounded shape, e.g. essentially as a semi-circular protrusion.

Further preferably, this latch is formed as a protruding portion of said wall, wherein typically for the envisaged applications the latch protrudes by at least 2 mm, preferably by at least 5 mm, most preferably in the range of 5-30 mm beyond the rest of the front edge, and/or wherein the latch has a circumferential length in the range of 5-90 mm, preferably in the range of 10-20 mm.

This latch is a very efficient tool for capturing the pouch. Typically, the pouches are provided lying on a surface and in a first step the opening of the pouch needs to be found and needs to be opened. To this end the latch is provided, in that the user grips the insertion tool on its backside end, and then uses the latch provided on the front side edge to slide below the upper layer of the opening of the pouch, then allowing to manually grab the edge of this upper layer of the opening of the pouch, and then the latch can be used for inserting the front portion of the insertion tool into the opening of the pouch in a controlled manner.

Preferably, there is provided one single latch, preferably on a side of the front side opening opposite to said axial slot, and wherein the rest of the front edge is shaped as an essentially straight edge.

According to yet another preferred embodiment, the front side opening has an elongated or oval shape (in a direction perpendicular to the axial direction), having a long width b and a short width c, preferably with rounded edges. Preferably said shape is elliptical, rectangular with rounded edges, or super elliptic with n>2.

Preferably, the long width is at least twice as large as the short width, preferably it is in the range of twice to 4 times as large as the short width.

Further preferably, the short width c is in the range of 5-50 mm, preferably in the range of 10-30 mm, and the long width b is in the range of 5-100 mm, preferably in the range of 30-70 mm.

Using these dimensions, the insertion tool is optimally adapted to the typical dimensions of the implantable devices and the corresponding pouches.

Further preferably, the wall of the insertion device has an elongated or oval shape viewed along an axial direction of the insertion tool, and the axial slot, at the narrowest point, has a circumferential width w of at least 2 mm, preferably in the range of 10-30 mm, most preferably in the range of 15-25 mm.

The provision of this slot is important on the one hand to provide for a certain flexibility of the device, but on the other hand in particular to allow the user to grip the edge of the pouch and to draw it over the front portion of the insertion device. Furthermore, the slot is important to allow for any wiring of the device to travel through that slot at the moment of releasing the pouch with the inserted implantable device from the insertion tool.

According to yet another preferred embodiment, the wall has an elongated or oval shape viewed along an axial direction of the insertion tool, and the axial slot is located on a long side of said wall, and on the opposite long side of said wall there is provided an axial cut-out from the backside opening. This axial cut-out provides for accessibility to the pouch when shifting it over the front portion of the device on the side opposite to the slot. Furthermore, it simplifies the insertion of the implantable device through the passage opening.

Preferably, the width of the axial cut-out is at least 2 mm, preferably in the range of 10-35 mm, most preferably in the range of 15-25 mm.

Typically, the insertion device it is made of a metal or plastic (including composites) material, preferably of a thermoplastic, thermoset material, or liquid rubbers. Also elastomers (in a rigid or semi-rigid form) or biodegradable cellulosic materials (e.g. single use eco-friendly cutlery type of materials) are possible. Preferably, the wall thickness is in the range of 0.3-4 mm, preferably in the range of 1-3 mm. The device can be produced in an injection moulding process, in an additive manufacturing (e.g. three-dimensional printing) process, or in a thermoforming process or metal inject moulding, sheet metal (bent, and/or laser cut, embossed), plastic welding (e.g. heat welding, ultrasonic welding). The part can be made in one single production step or in several steps. (e.g. additional surface refinement). Possible materials are, e.g. in the form of polymer sheets, polyamide, polyester, ABS, POM, polyethylene, polypropylene, fluorinated aliphatic polymers (e.g. PTFE), EPDM, PEEK/PEAK, silicones as well as copolymers or mixtures thereof. Preferably, the material is sterilisable and intended for single or multiple use. The material of the insertion device can also be a multilayered material. Further it can be coated with the same or one or several additional materials.

According to yet another preferred embodiment, the wall can have an elongated or oval shape viewed along an axial direction of the insertion tool, and the axial slot is located on a long side of said wall. On the opposite long side of said wall there can be provided an axial cut-out from the backside opening, separating the insertion tool into a latch portion and a wing portion. The latch portion carries a latch (preferably as defined above) axially protruding beyond a front edge of the front side opening, preferably with rounded shape, and the wing portion, on the back portion of the device comprises at least one, preferably at least two wide wing portions, joined in case of two wing portions by a saddle portion, said wing portions extending axially over and beyond the rest of the backside edge of the backside opening and widening the funneled wall. These wing portions allow the user to hold and grip the insertion tool optimally for the different stages of manipulation.

The wall of the device can be in the form of a single contiguous structure, it can however also have openings, so it can be a porous wall or the wall may also be hollow or may be formed by a grid or a mesh structure, which can be rigid, semi-rigid and/or elastic. The wall may further be formed by a single layer of one same material or of a material mixture, or it may be formed by a multilayer structure. Also the wall may take the form of a composite, in which certain portions are made from a first material, and other portions from another second material, e.g. said first material being a fully rigid material and the second an elastic material.

The outer surface of said wall at least in a front portion can be structured (roughness, texture, surface topology), may comprise external activated components such as piezo elements, or may be provided with a coating or made of a material providing static friction when interacting with the pouch, in particular when for example interacting with the cellulose-based pouch.

Preferably, the wall of the insertion tool is tubular or funneled, in the latter case widening the passage opening from the front side opening to the backside opening. Preferably, the opening angle of the funneled wall is in the range of 0-50°, preferably in the range of 30-45°. This angle can be the local angle but it can also be the average angle over the full height of the device, and the angle is typically taken in a front view and/or in a side view, and is taken with respect to the tip of the wide wing portions. The shape can also be trumpet like, i.e. the opening angle can be increasing when travelling from the front side opening to the backside opening. In this case the above-mentioned opening angle is the average angle. Furthermore, and particularly preferably, in the front most portion of the wall it can have an essentially parallel wall structure, which, after a height of typically around 3-5 mm, gradually starts widening until reaching opening angle in the range of 20-40°, and then stays at this constant opening angle until the backside edge. Further preferably, the wall has an elongated or oval shape viewed along an axial direction of the insertion tool, and along the long axis b the widening is at least by a factor of 1.5, preferably in the range of 1.7-2.5, and along the short axis c the widening is at least by a factor of 2, preferably in the range of 2-5, most preferably in the range of 3-4.5.

According to yet another preferred embodiment, the insertion tool is foldable from a folded state, in which it is preferably essentially flat or at least in a compact form, to an unfolded state, in which it can be used as an insertion tool, wherein preferably the fold ability is provided by a corresponding material choice (elastic) and/or correspondingly elastic portions and/or by foldable portions, preferably comprising film hinges and/or by providing the layer of the wall as a grid or mesh having elastic properties. Possible are further auxetic structures or origami type like structures, compliant mechanisms, inflatable structures, kirigami, active self-deploying structures, sequential self-folding of polymer sheets or combinations thereof.

The unfolding can start from an essentially flat compressed configuration, allowed by corresponding elastic regions, or it can start from a more compact configuration, e.g. starting off from a configuration where the axial slot is essentially closed or where the sidewalls are even overlapping in the region of the axial slot, and unfolding that structure to the final insertion tool having an axial slot of the desired width.

Unfolding can take place without active interaction of the user, for example by providing elastic material and/or form shape memory material which is compressed in the folded state, and/or it can be initiated and/or supported actively for unfolding by manual gripping parts of the insertion tool, or by the use of specific expansion tools, which can be separate parts or parts of the insertion tool. These expansion tools can be given by mechanical push or pull mechanisms, e.g. by a compliant lever mechanism, or by inflatable structures, which are preferably part of the insertion tool or which can be firmly attached to the insertion tool. The latter inflatable structures can be realised by providing a bellow as a tool which can be manually actuated by the user and the compressed air of which is used for expanding the insertion tool to the folded structure. To this end hollow parts or regions (if needed including pneumatic distribution system) can be provided in or associated with the structure which have a low internal volume in the folded state and a higher internal value in the unfolded state, and which can preferably be associated with or provided in elastic regions of the insertion tool to provide for the unfolding property. The bellow can be part of the insertion tool or it can be a separate part which can be attached to a corresponding tube or connecting element provided at the insertion tool. Such an inflatable structure may also comprise valves, in particular valves which keep the insertion tool in the expanded state until the valve is released, e.g. manually by the user for folding and delivery.

The folding and unfolding can be used on the one hand to provide for a storage configuration in the folded state, however it can also be used for using the folded or more compact mode as a delivery mode, having a smaller outer circumference at the front opening allowing to release a pouch, and an expanded or inflated or activated unfolded mode for attaching the pouch at the front opening and keep it in place for bringing to the position where delivery shall take place.

Furthermore, the present invention relates to the use of an insertion tool having a wall of essentially tubular or funneled shape, and having, on a front portion thereof, a front side opening suitable and adapted so that an opening of an empty pouch for an implantable pulse generator, and, if present, corresponding wiring, can at least partially be shifted onto said front portion and over said front side opening, and having, on a back portion of the insertion tool, a backside opening suitable and adapted so that an implantable pulse generator, and, if present, corresponding wiring, can be inserted through that backside opening, through a passageway opening to the front side opening and into said pouch, while manually holding the insertion tool using said back portion, preferably of an insertion tool as described above, for inserting an implantable pulse generator into a pouch.

Preferably said wall comprises an axial slot between the front side opening and the backside opening.

Further, the present invention relates to a method for inserting an implantable pulse generator into a pouch. Preferably, such a pouch is a biodegradable, biocompatible and/or protecting pouch, further preferably a single piece pouch made of preferably biosynthesized cellulose. The proposed method makes use of an insertion tool having a wall of essentially tubular or funneled shape, and having, on a front portion thereof, a front side opening, and having, on a back portion of the insertion tool, a backside opening, wherein preferably said wall comprises an axial slot between the front side opening and the backside opening. According to this method, in a first step an opening said empty pouch is at least partly shifted onto said front portion and over said front side opening. Preferably during this first step the latch is used as an aid for opening the pouch, and the slot as well as the cut-out are used to grab the front edge of the opening of the pouch to droid over the front portion of the tool as far up as necessary and appropriate.

In a second step an implantable pulse generator and, if present, corresponding wiring, is inserted through that backside opening, through a passageway opening to the front side opening and into said pouch, preferably while manually holding the insertion tool using said back portion.

In a final step the pouch with the implantable pulse generator, and, if present, corresponding wiring, is released from the insertion tool. This is made particularly simple due to the presence of the axial slot as well as, preferably, of the axial cut-out on the opposite side of the axial slot. The filled pouch is now ready for being implanted.

Further embodiments of the invention are laid down in the dependent claims.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

a side view in the delivery mode or in a compact state is shown, and in c) a front view and in b) a side view in the activated or expanded mode.

DESCRIPTION OF PREFERRED EMBODIMENTS

Figure 1:
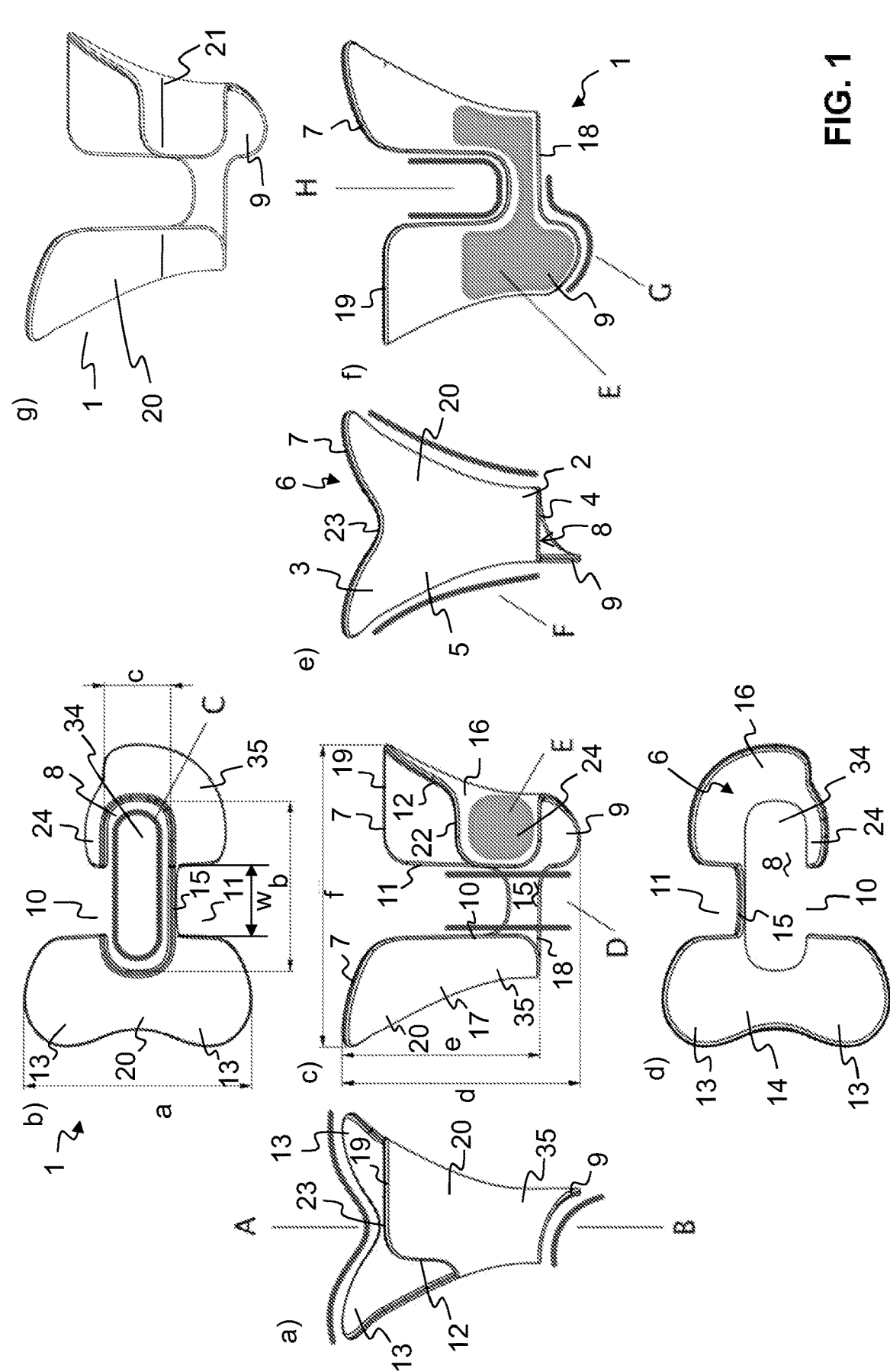
FIG. 1 shows an insertion tool in various representations, specifically in a) a right side view, in b) in a bottom view, in c) in a front view, in d) in a top view, in e) in a left side view, in f) in a back view, and in g) the same view as given in c) but for an embodiment with a horizontal line on the outer surface.

FIG. 1, in particular a)-f), shows a first embodiment of an insertion tool 1 in various different representations. The insertion tool 1 comprises a front portion 2 and a back portion 3. Between those two portions, there is a central portion 5.

The actual single wall 35 of the device is forming the insertion tool by providing a backside opening 6 defined by a backside edge 7, and a front side opening 8 defined by a front edge 4. The front side opening 8 mainly comprises a straight edge 18 but, importantly, in a portion opposite to an axial slot 10, it comprises a latch 9, which axially protrudes beyond the straight portion 18.

This latch 9 has a rounded shape and it is provided only on the latch portion 16 of the insertion tool.

The insertion tool has an axial slot 10 which makes the passageway 34 between the backside opening 6 and the front side opening 8 accessible laterally along the full axial length of the device. Opposite to that axial slot 10 there is provided an axial cut-out 11, which extends from the backside opening 6 towards the front side opening 8. This axial cut-out 11 forms a connecting portion 15, connecting the above-mentioned latch portion 16 of the insertion tool with the wing portion 17 of the insertion tool.

The wing portion 17 is wider than the latch portion 16 in the back portion and comprises, in the back portion, two wide wing portions 13 between which there is a saddle portion 23. These wide wing portions 13 on the one hand emphasize the funnel or trumpet like shape of the device and simplify the insertion of the implantable device, and on the other hand significantly also simplify the handling of the device as will be detailed further below.

The latch portion 16 on the side of the slot 10 further comprises a backside widening 12 in the direction of the backside opening 6. This provides a saddle portion 22 and further simplifies access to the pouch when drawing it over the front edge and the front portion of the tool.

The wall has an inner surface 14 and an outer surface 20. On the outer surface there can be provided particular areas E to create static fraction to hold the pouch during the insertion of the implantable device. For example, these areas can be provided on a tab portion 24 formed between the slot 10 and the settle portion 22. Creating static friction can take place by way of surface structuring (texturing, ribbing, three-dimensional topology, et cetera) or by a particular adhesive coating or choice of the material in the surface region.

The particular grip shape given by a wide wing portion 13 and the saddle portion 23 between them is particularly highlighted by way of the line indicated with A in FIG. 1.

The smooth form of the latch 9 is further highlighted by way of the line indicated with B in FIG. 1.

The shape of the front side opening 8 is adapted and optimized in its form to the intended implantable device in particular with rolled up electrodes, as is illustrated by the schematic line C in FIG. 1.

The slot 10 is illustrated by the two vertical lines in the representation in FIG. 1c) and is designated with D. This slot 10 is provided for the electrode/wiring and to provide close access to the pouch and the body.

In FIG. 1e) by way of the lines illustrated with F, the cone or funnel or trumpet shape is emphasized, which is helping to spread the pouch open when shifting it over the front portion 2 and to simplify insertion of the implantable device.

The latch 9 is further highlighted by the line G in FIG. 1f), the latch 9 is provided for easy access for the pouch and finding/preparing the opening for the pouch shifting it over the front portion of the device.

Finally, yet importantly, the axial cut-out is illustrated in figure f) providing access to the pouch to pull it up with plyers or manually.

Such an insertion tool can be provided separately, it can however also be provided together with a corresponding pouch already mounted on and can be packed together with a corresponding pouch. In this case, the end user (clinician) opens the corresponding package and simply has to insert the implantable device into a pouch, which is already mounted on the insertion tool.

Figure 2:
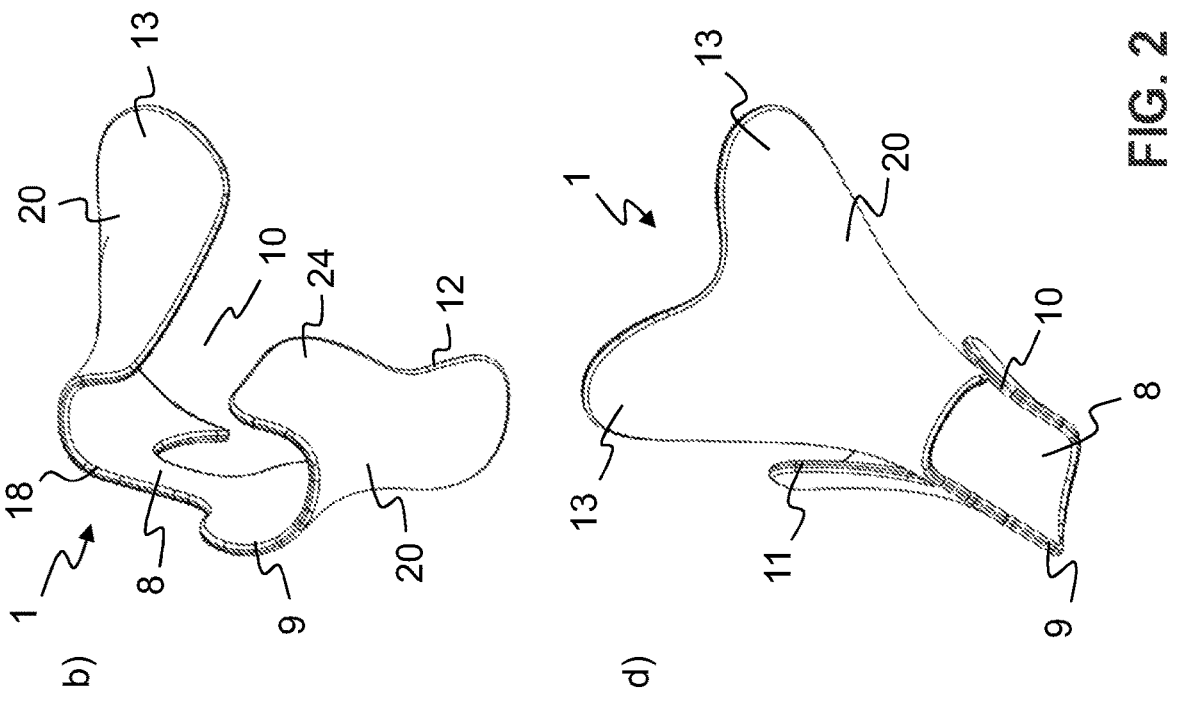
FIG. 2 shows the insertion tool of FIG. 1 in different perspective representations, specifically in a) a top view from the backside, in b) a bottom view from the front side, in c) a right side view from the top, and in d) a bottom left side view.
Figure 2:
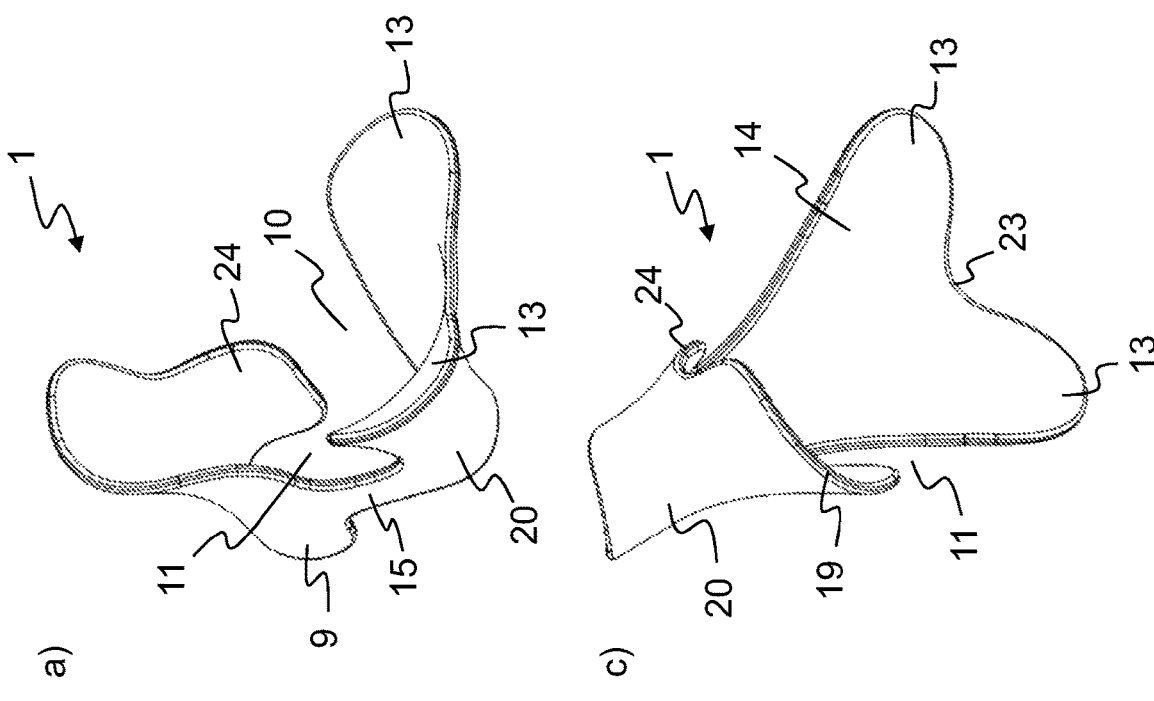

FIG. 2 shows the same pouch as illustrated in FIG. 1 in several different perspective representations to visualize the shape of the device.

In all the figures, the same or similar parts are designated with the same reference numerals.

Figure 3:
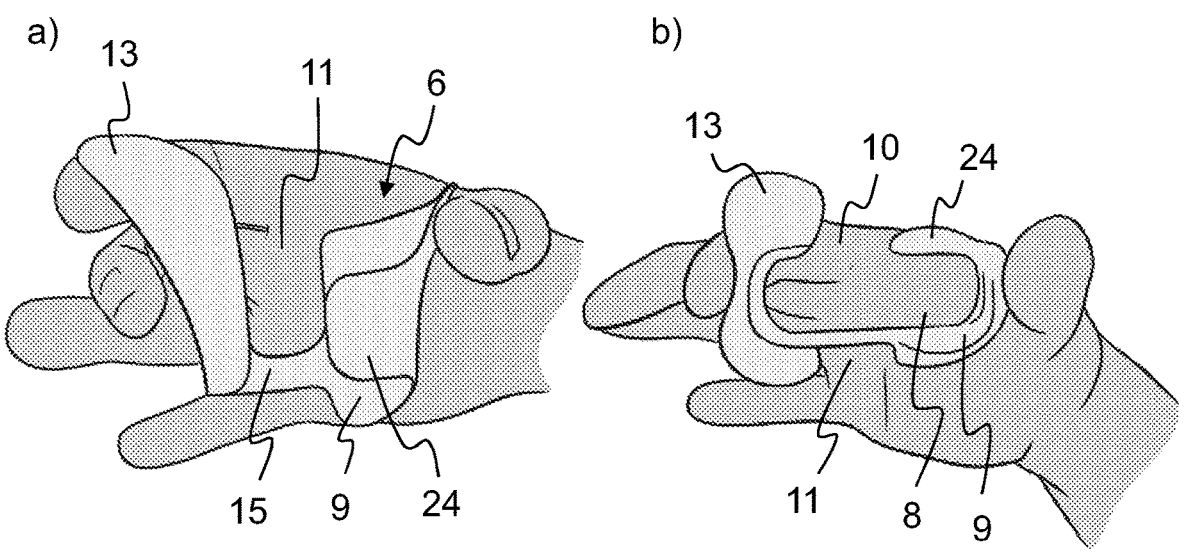
FIG. 3 shows a hand holding the insertion tool in different ways, specifically in a) in an embracing longitudinal holding position, in b) in a top longitudinal holding position, in c) in a single side gripping position, and in d) in a top clamping position.
Figure 3:
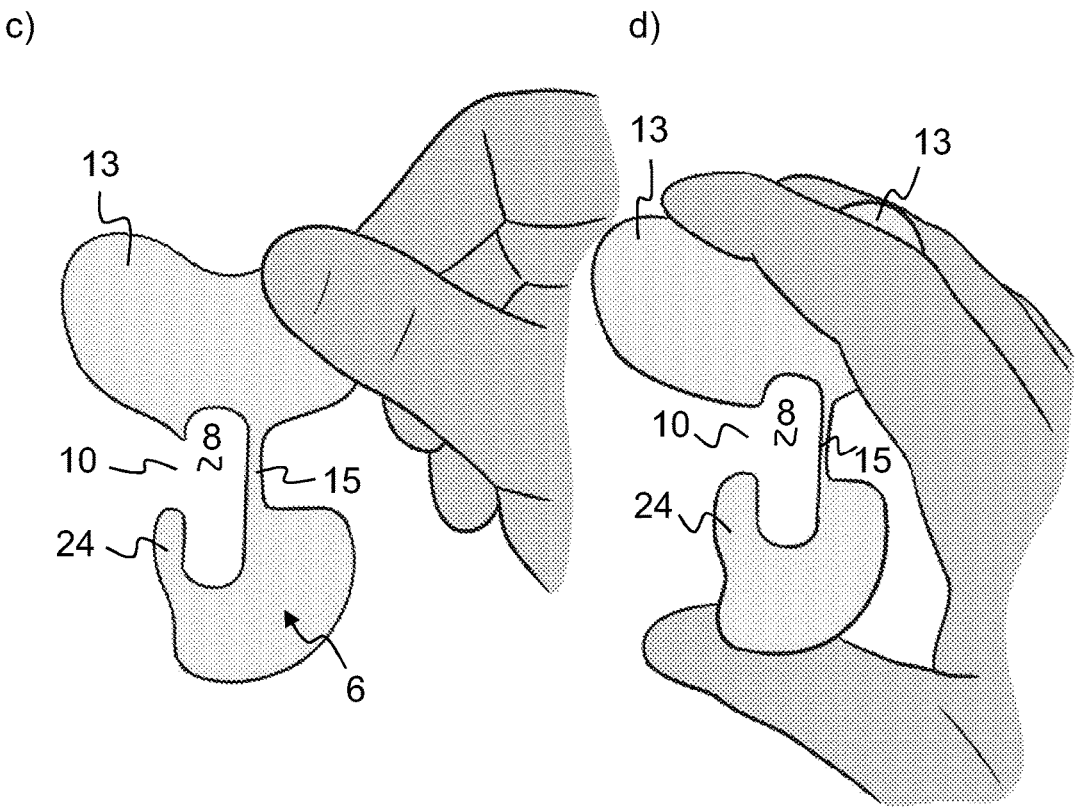

FIG. 3 illustrates different suitable holding positions of the device during the manipulations.

In FIG. 3a) a first holding position is illustrated, typically the one which is used at the moment when the implantable device is inserted into the pouch by shifting it through the backside opening of the insertion tool. I.e. in this case the pouch is typically mounted already on the insertion tool.

FIG. 3b) illustrates the typical holding position at the moment when the pouch in its empty state is lying on a surface and the opening shall be found and opened by using the latch 9. The holding position as illustrated in FIG. 3c) is typically the one, which is used during the process of shifting the empty pouch onto the front portion of the insertion tool. In this case the right hand can grab the insertion tool on one of the wide wing portions 13, and the other hand can be used to shift the pouch as far as possible upwards on the device and to fix it on the front portion 2 of the device.

The holding position according to FIG. 3d) is similar to the one as illustrated in FIG. 3a) and is suitable for the same process steps, however it provides an even better alternative with very stabilized holding.

Figures 4, 5:
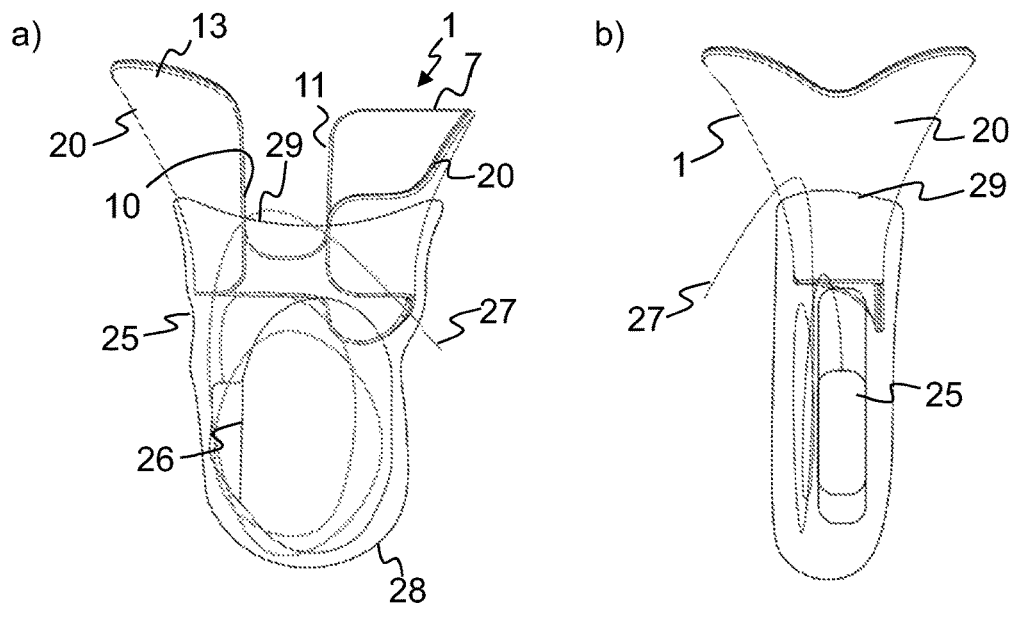
FIG. 4 shows the insertion tool with a pouch containing a cardiovascular implantable electronic device, in a) in a front view, and in b) a right side view.
FIG. 5 shows an insertion tool with specific scaling areas, wherein in a) a bottom view is given, in b) a front view, and in c) a left side view.

FIG. 4 in a) illustrates the situation when the pouch 25 is mounted on the insertion tool 1 and has already been filled with an implantable device 26, and where the wiring/electrode 27 of the implantable device protrudes out of the opening 29 of the pouch. As one can see from this representation, the leading of the wiring 27 out of the pouch 25 is one of the reasons for the axial slot 10 in the insertion tool.

In FIG. 4b) the same is illustrated in a side view.

As one can see from these representations, the pouch is shifted upwards on the insertion tool quite far. In order to give a guideline how far the pouch shall be shifted on to the insertion tool, specific horizontal lines 21 (see also FIG. 1g) can be provided on the outer surface of the device.

In FIG. 5 a second embodiment is shown, which has been scaled to provide help with another size of pouch/implantable device having different dimensions. In the manufacturing process, the scaling can be simplified by providing corresponding adaptable scaling areas, which are preferably provided in both dimensions, namely a lateral scaling area 30', can be provided along the short access of the opening, and along the two scaling area 30" can be provided on the long axis.

The dimensioning of the corresponding device (see in particular the illustrations in FIGS. 1*b*) *c*)) is for example chosen to be a=45-65 mm, b=45-55 mm, c=10-20 mm, d=60-75 mm, e=50-70 mm, f=75-90 mm, w=10-20 mm.

Figures 6, 7:
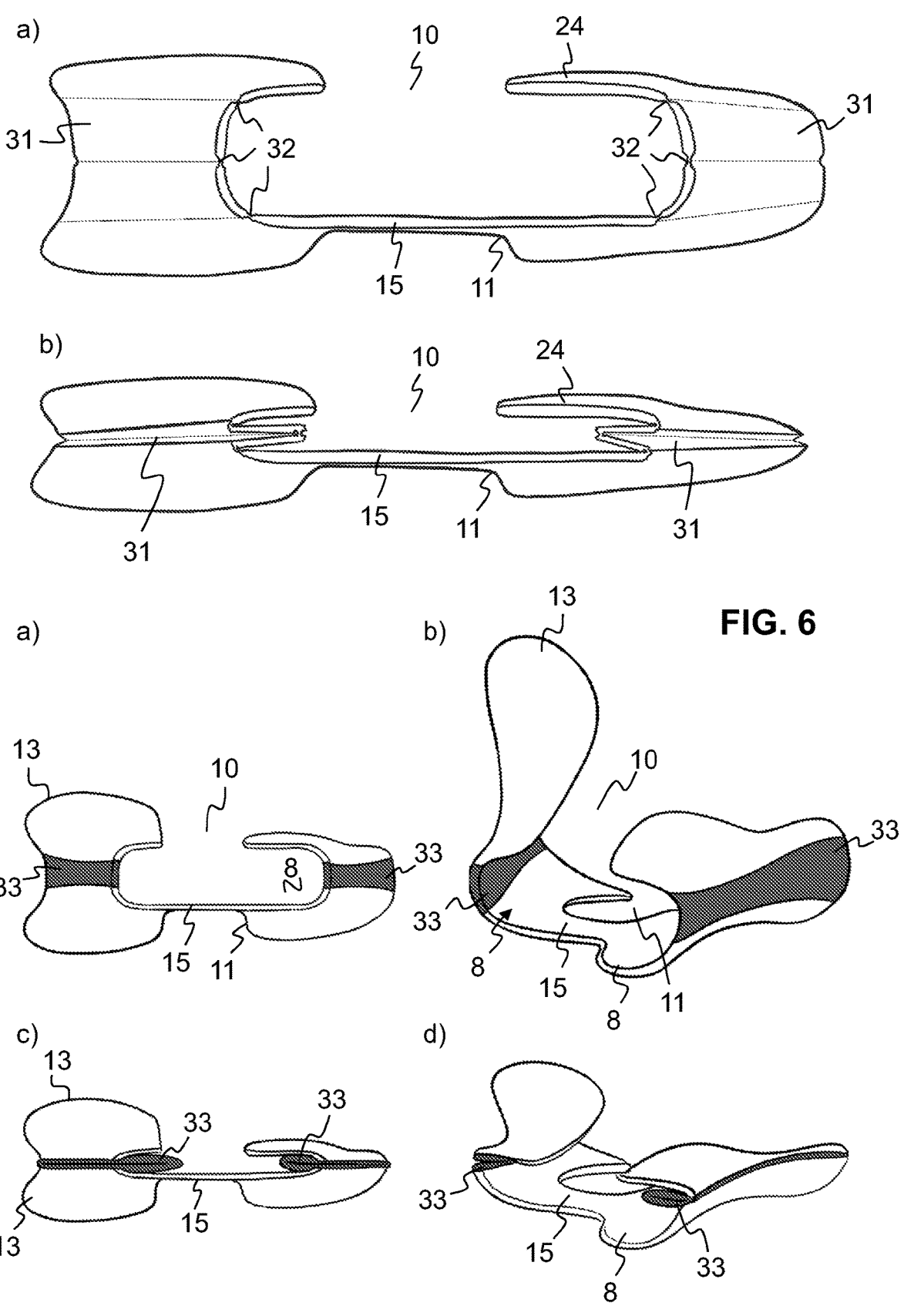
FIG. 6 shows a foldable insertion tool in bottom views, wherein in a) the unfolded situation is given and in b) the folded situation.
FIG. 7 shows an elastic flexible insertion tool, wherein in a) a bottom view of the unfolded state is given, in b) a perspective representation of the front from the bottom of the unfolded state, in c) a bottom view of the folded state, and in d) a perspective representation of the front from the bottom of the folded state.

As illustrated in FIG. 6, it is also possible to provide the insertion tool as a foldable tool. To this end, in the lateral scaling areas as discussed in the context of FIG. 5, there is provided a folding area 31 with three axial film hinges 32 or with multipart mechanical hinges.

As one can see from the unfolded (a) and the folded (b) representations, this design allows to compress the shape to an essentially flat form, which in particular may be useful for sterilizing purposes, or also for packaging purposes, of if the pouch is to be supplied together with the insertion tool in a package.

An alternative version of a foldable insertion tool is illustrated in FIG. 7, here a flexibility is provided by corresponding elastic flexible areas 33. These elastic flexible areas can be provided by way of a composite or two-component injection moulding process, in which a stiff material is provided for shaping all those areas except the dark ones, while the dark ones are made from a soft flexible elastic material. Like this, the shape of the insertion tool can be compressed as illustrated in this figure. The flexible areas can also be made of a compliant mechanism, inflatable structure, kirigami, active self-deploying structures, or external activated elements such as Sequential Self-folding of Polymer Sheets or piezo elements.

During the actual use of the insertion tool, essentially the following manipulations are carried out:

In a first step the tool is grasped basically as illustrated in FIG. 3*b*).

A pouch lying on a surface is then accessed by using the latch and by insertion the latch into the opening of the empty pouch, lifting the upper layer of the pouch up such that the other hand of the user can grab this upper layer and shift it over the front portion of the front opening. This can in particular take place in the area of the axial slot.

Then the tool can be rotated and the pouch can be drawn over the front portion also in the backside area, by using the axial cut-out.

In the next step, the implantable device can be inserted via the backside opening through the passageway into the pouch.

Then the pouch with the implantable device inserted into it can be released from the insertion tool.

Figure 8:
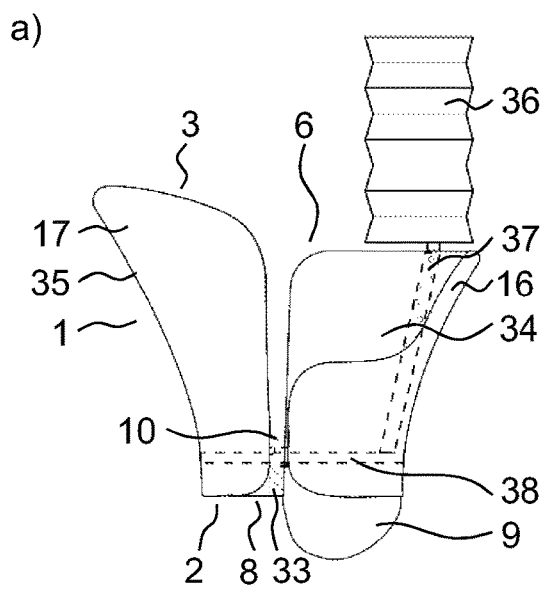
FIG. 8 shows an insertion tool which can be unfolded by a pneumatic mechanism, wherein in a) a front view and in b) a side view in the delivery mode or in a compact state is shown, and in c) a front view and in b) a side view in the inflated mode.
Figure 8:
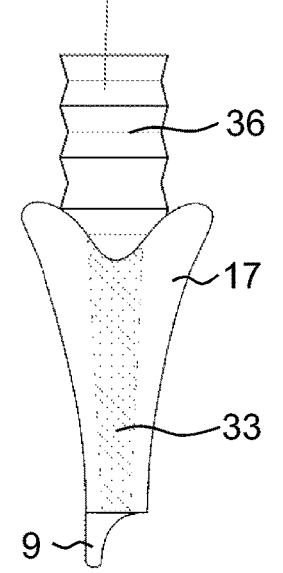
Figure 8:
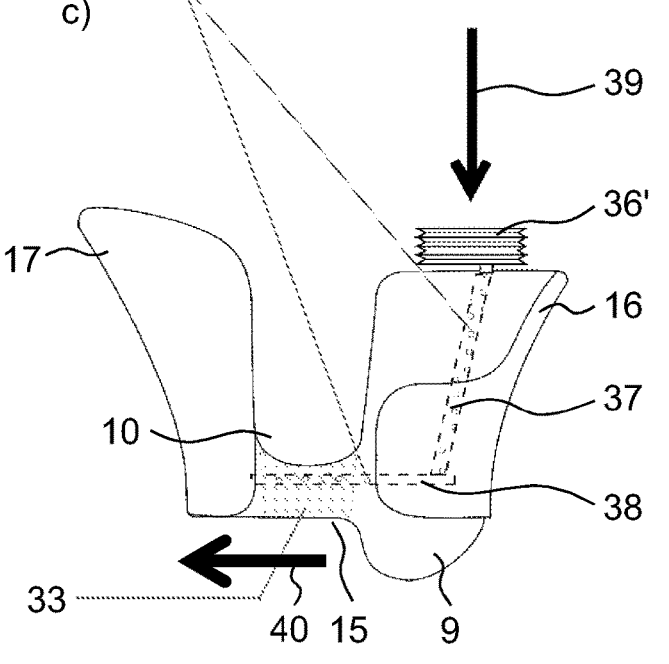
Figure 8:
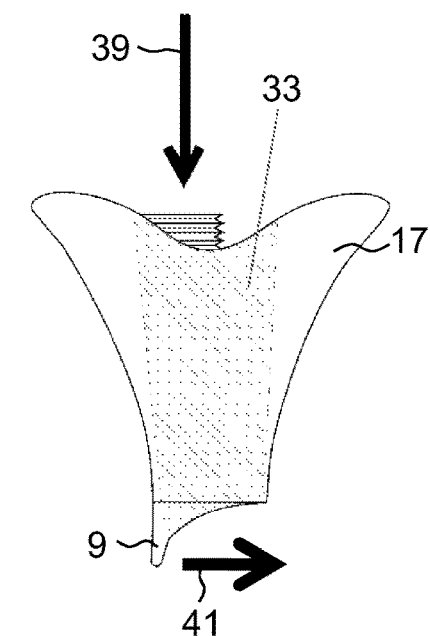

FIG. 8 shows a further embodiment of the proposed insertion tool 1. In a) a front view and in b) the side view of the more compact folded or uninflated state for delivery is shown. The insertion tool 1 again comprises the wing portion 17 and the latch portion 16, between which there is a connecting portion 15. The connecting portion in this embodiment is structured as a flexible or expandable structure 33. Also flexible or expandable is an area within the wing portion and extending in an axial direction as visible in b). Also at the opposite side in the latch portion a corresponding flexible or expandable structure 33 is provided.

The insertion tool 1 comprises pneumatic system with the following elements: there is provided an air container which is compressible, i.e. a bellow 36 which can be activated by the user. This bellow is connected by air channels 37 to a portion 38, in this case a circumferential portion in the front region, of an expansion channel. The expansion channel is arranged across the flexible or expandable structure 33 in the connecting portion 15 as well as across the flexible or expandable structure 33 in the wing portion 17.

Figure 9:
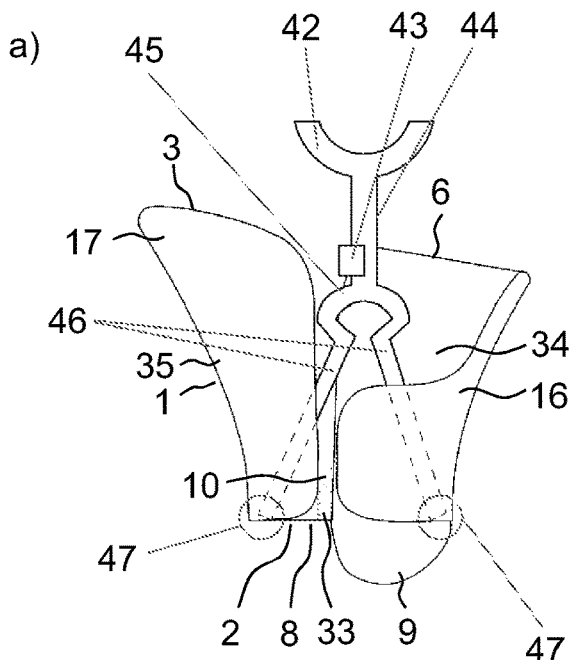
FIG. 9 shows an insertion tool which can be unfolded by a compliant mechanism, wherein in a) a front view and in b)
Figure 9:
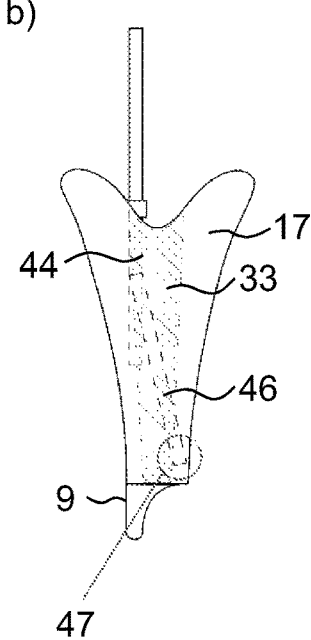
Figure 9:
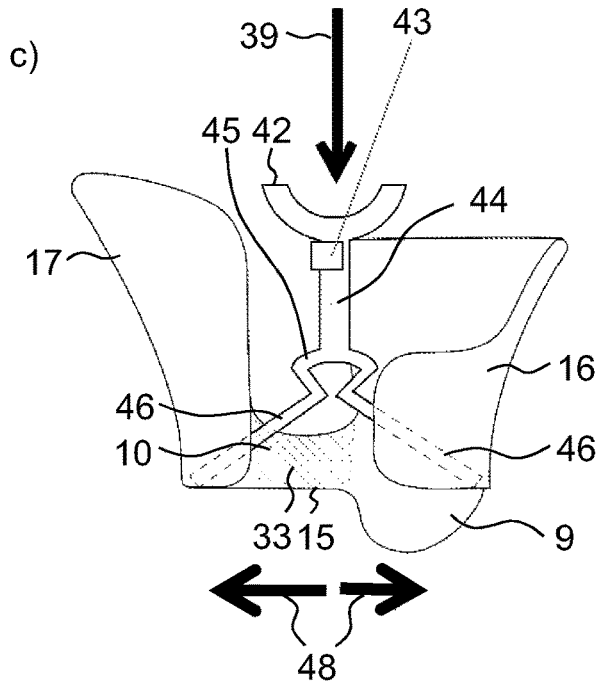
Figure 9:
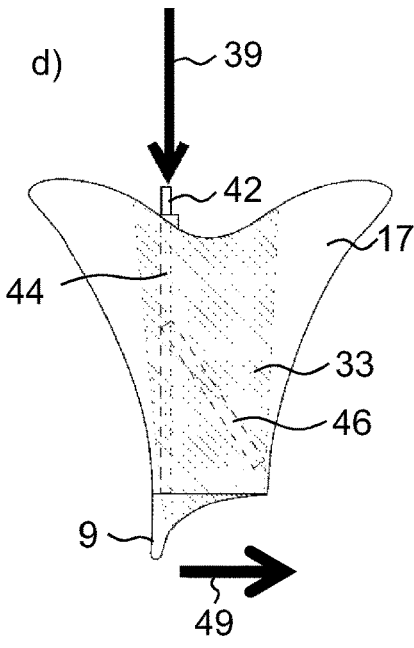

Figure c) and d) show front view and side view, respectively, of an inflated state of this insertion device 1. The user has pushed on top of the bellow 39 as illustrated by arrow 39, increasing the pressure in the pneumatic distribution system 37 and correspondingly also in the circumferential portion 38 of that channel system. Correspondingly the flexible/expandable structures 33 in the connecting portion 15 as well as in the wing portion 17 and the latch portion 16 are expanded due to the increased pressure in the circumferential portion 38 of the pneumatic distribution system, leading to a much larger width of the slot 10. In other words activation or actuation of the bellow 36 can be used to adjust the width of the slot and corresponding the circumferential width of the front opening 2. For engaging the pouch by way of its inner circumference of the opening portion the insertion tool can be inserted in the uninflated state and can be inflated to the inflated state thereby engaging the outer circumference of the front portion 2 with the inner surface of the opening side of the pouch. In particular if the corresponding valve is provided blocking exit of air from the distribution system, this state is then fixed for bringing the insertion tool with the pouch to the desired place, and the pouch, with a corresponding content, can be released by releasing the valve or by, in the absence of a valve, releasing the bellow. Another expandable structure not using pneumatic but a mechanical expansion system as illustrated in FIG. 9. In this case expansion is initiated by a mechanical construction comprising a push area 42 linked to a rigid link 44, which is guided and held in a guide element 43 on the latch portion. At the lower end the rigid link 44 is connected to a flexible joint portion 45, from which to rigid arm portions 46 extend downwards 2 connection points 47 at the side of the device opposite to the side where the guide element 43 is provided. Also in this case, the connecting portion 15 as well as both the latch portion 16 and the wing portion 17 are provided with axial flexible and/or expandable areas 33. To bring the insertion device from the compact or delivery state illustrated in a) and b) to an activated or expanded mode as illustrated in c) and d), the user pushes the push area 42 to lower the rigid link 44, thereby pushing apart the bottom ends of the two arms 46 around the flexible joint portion 45 and expanding the device on the one hand by opening the axial slot 10 in the direction as illustrated by the arrows 48, but on the other hand also widens the device as illustrated by the arrow 49.

While in this embodiment activation takes place by pushing in an axial direction, the same is also possible by providing a corresponding mechanism allowing to activate in a lateral direction or in the oblique direction expanding the device in a similar or the same way as illustrated in FIG. 9.

| | LIST OF REFERENCE SIGNS |
|---|---|
| 1 | insertion tool |
| 2 | front portion |
| 3 | back portion |
| 4 | front edge |
| 5 | central portion |
| 6 | backside opening |
| 7 | backside edge |
| 8 | front side opening |
| 9 | latch |
| 10 | axial slot |
| 11 | axial cut-out |
| 12 | backside widening of 10 |
| 13 | wide wing portions |
| 14 | inner surface |

-continued

LIST OF REFERENCE SIGNS

| | |
|---|---|
| 15 | connecting portion |
| 16 | latch portion |
| 17 | wing portion |
| 18 | straight portion of 4 |
| 19 | straight portion of 7 |
| 20 | outer surface |
| 21 | horizontal line on outer surface |
| 22 | saddle portion of 12 |
| 23 | saddle portion between 13 |
| 24 | tab portion |
| 25 | pouch |
| 26 | cardiovascular implantable electronic device |
| 27 | cable |
| 28 | closed bottom of pouch |
| 29 | opening of pouch |
| 30 | scaling area |
| 30' | lateral scaling area |
| 30" | longitudinal scaling area |
| 31 | treble folding area |
| 32 | film hinge |
| 33 | (elastic) flexible area |
| 34 | passage opening |
| 35 | wall |
| 36 | air container, bellow |
| 36' | compressed bellow |
| 37 | pneumatic distribution system, air channel, hollow pneumatic distribution structure |
| 38 | at least partly circumferential portion of 37 |
| 39 | activation push by the user |
| 40 | opening direction opening the slot |
| 41 | widening direction |
| 42 | push area |
| 43 | guide element |
| 44 | rigid link |
| 45 | flexible joint portion |
| 46 | rigid arm portions |
| 47 | connection point |
| 48 | slot widening direction |
| 49 | widening direction |
| a | width of wide wing portion |
| b | long width of front side opening |
| c | short width of front side opening |
| d | height of insertion tool |
| e | height of wide wing portion |
| f | length of back portion |
| w | width of the slot |
| A | grip shape |
| B | smooth form to pull the pouch onto |
| C | optimized form for CIEDs with rolled-up electrodes |
| D | front cut-out for the electrode and close access to the body |
| E | areas to create static friction to hold the pouch while the insertion of the CIED |
| F | cone shape to spread the pouch open |
| G | latch for an easy access to the pouch and finding/preparing the opening |
| H | partly cut-out on the backside gives access to the pouch to pull it up with pliers |
| CIED | Cardiac Implantable Electronic Device |
| IPG | Implantable Pulse Generator |

The invention claimed is:

1. An insertion tool having a wall,
comprising, on a front portion of the insertion tool, a front side opening configured so that an opening of an empty pouch for an implantable pulse generator can be shifted onto said front portion and over said front side opening, and
comprising, on a back portion of the insertion tool, a backside opening configured so that an implantable pulse generator can be inserted through that backside opening, through a passageway opening to the front side opening and into said pouch, while manually holding the insertion tool using said back portion,
wherein said wall comprises an axial slot between the front side opening and the backside opening; and
wherein the wall has a funnel shape, widening the passage opening from the front side opening to the backside opening.

2. The insertion tool according to claim 1, wherein at said front side opening there is provided a latch axially protruding beyond a front edge of the front side opening.

3. The insertion tool according to claim 2, wherein there is provided one single latch.

4. The insertion tool according to claim 2, wherein the latch has a circumferential length in the range of 5-90 mm.

5. The insertion tool according to claim 2, wherein there is provided one single latch, on a side of the front side opening opposite to said axial slot, and wherein the rest of the front edge is shaped as an essentially straight edge.

6. The insertion tool according to claim 2, wherein the latch has a circumferential length in the range of 10-20 mm.

7. The insertion tool according to claim 1, wherein the front side opening has an elongated or oval shape, having a long width and a short width.

8. The insertion tool according to claim 1, wherein the wall has an elongated or oval shape viewed along an axial direction of the insertion tool, and wherein the axial slot, at the narrowest point, has a circumferential width of at least 2 mm.

9. The insertion tool according to claim 1, wherein the wall has an elongated or oval shape viewed along an axial direction of the insertion tool, and wherein the axial slot is located on a long side of said wall, and wherein on the opposite long side of said wall there is provided an axial cut-out from the backside opening.

10. The insertion tool according to claim 1, wherein the insertion tool is made of a metal or plastic material,
and/or wherein the wall is a contiguous or perforated wall.

11. The insertion tool according to claim 1, wherein the wall thickness is in the range of 0.5-4 mm.

12. The insertion tool according to claim 1, wherein the wall has an elongated or oval shape viewed along an axial direction of the insertion tool, and wherein the axial slot is located on a long side of said wall, and wherein on the opposite long side of said wall there is provided an axial cut-out from the backside opening, separating the insertion tool into a latch portion and a wing portion, wherein the latch portion carries a latch axially protruding beyond a front edge of the front side opening, and wherein the wing portion, on the back portion comprises at least one wide wing portions, joined by a saddle portion, extending beyond the rest of the backside edge of the backside opening and widening the funneled wall.

13. The insertion tool according to claim 1, wherein the outer surface of said wall at least in a front portion is structured or provided with a coating or made of a material providing static friction when interacting with the pouch.

14. The insertion tool according to claim 1, wherein at said front side opening there is provided a latch axially protruding beyond a front edge of the front side opening, with rounded shape, wherein this latch is formed as a protruding portion of said wall.

15. The insertion tool according to claim 14, wherein the latch protrudes by at least 2 mm beyond the rest of the front edge.

16. The insertion tool according to claim 14, wherein the latch protrudes in the range of 5-30 mm beyond the rest of the front edge.

17. The insertion tool according to claim 1, wherein the front side opening has an elongated or oval shape, having a long width (b) and a short width (c), with rounded edges, or wherein said shape is elliptical, rectangular with rounded edges, or super elliptic with n>2.

18. The insertion tool according to claim 17, wherein the long width of the shape is at least twice as large as the short width, and/or wherein the short width (c) of the shape is in the range of 5-50 mm, and the long width (b) is in the range of 5-100 mm.

19. The insertion tool according to claim 17, wherein the long width of the shape is in the range of twice to 4 times as large as the short width, and/or wherein the short width (c) of the shape is in the range of 10-30 mm, and the long width (b) is in the range of 30-70 mm.

20. The insertion tool according to claim 1, wherein the wall has an elongated or oval shape viewed along an axial direction of the insertion tool, and wherein the axial slot, at the narrowest point, has a circumferential width (w) in the range of 10-30 mm.

21. The insertion tool according to claim 1, wherein the wall has an elongated or oval shape viewed along an axial direction of the insertion tool, and wherein the axial slot is located on a long side of said wall, and wherein on the opposite long side of said wall there is provided an axial cut-out from the backside opening, wherein the width of the axial cut-out is at least 2 mm.

22. The insertion tool according to claim 1, wherein the wall thickness is in the range of 1-3 mm.

23. The insertion tool according to claim 1, wherein the wall has an elongated or oval shape viewed along an axial direction of the insertion tool, and wherein the axial slot is located on a long side of said wall, and wherein on the opposite long side of said wall there is provided an axial cut-out from the backside opening, separating the insertion tool into a latch portion and a wing portion, wherein the latch portion carries a latch axially protruding beyond a front edge of the front side opening, with rounded shape, and wherein the wing portion, on the back portion comprises at least one, or at least two wide wing portions, joined by a saddle portion, extending beyond the rest of the backside edge of the backside opening and widening the funneled wall.

24. The insertion tool according to claim 1, wherein the outer surface of said wall at least in a front portion is structured or provided with a coating or made of a material providing static friction when interacting with the cellulose-based pouch.

25. The insertion tool according to claim 1, wherein the wall is funneled, widening the passage opening from the front side opening to the backside opening, wherein the wall has an elongated or oval shape viewed along an axial direction of the insertion tool, and along the long axis (b) the widening is at least by a factor of 1.5, and along the short axis (c) the widening is at least by a factor of 2.

26. The insertion tool according to claim 1, wherein the wall has an elongated or oval shape viewed along an axial direction of the insertion tool, and wherein the axial slot, at the narrowest point, has a circumferential width (w) in the range of 15-25 mm.

27. The insertion tool according to claim 1, wherein the front side opening is configured so that corresponding wiring of the implantable pulse generator also can be shifted onto said front portion and over said front side opening, and wherein the backside opening is configured so that corresponding wiring of the implantable pulse generator also can be inserted through that backside opening, through a passageway opening to the front side opening and into said pouch, while manually holding the insertion tool using said back portion.

28. An insertion tool having a wall having a tubular or funnel shape, comprising, on a front portion of the insertion tool, a front side opening configured so that an opening of an empty pouch for an implantable pulse generator can be shifted onto said front portion and over said front side opening, and comprising, on a back portion of the insertion tool, a backside opening configured so that an implantable pulse generator can be inserted through that backside opening, through a passageway opening to the front side opening and into said pouch, while manually holding the insertion tool using said back portion, wherein said wall comprises an axial slot between the front side opening and the backside opening, and wherein the insertion tool is foldable from a folded state to an unfolded state, in which the insertion tool can be used as an insertion tool.

29. The insertion tool according to claim 28, wherein the wall has a funnel shape, widening the passage opening from the front side opening to the backside opening.

30. The insertion tool according to claim 28, wherein the fold ability is provided by a corresponding material forming the wall and/or the type of the wall, by providing the wall as a grid or mesh, and/or by correspondingly elastic portions and/or by foldable portions, comprising film hinges.

31. A method comprising inserting an implantable pulse generator into a pouch with an insertion tool according to claim 1.

32. The method according to claim 31, wherein in a first step an opening of said empty pouch is at least partly shifted onto said front portion and over said front side opening, wherein in a second step an implantable pulse generator is inserted through the backside opening, through a passageway opening to the front side opening and into said pouch, while manually holding the insertion tool using said back portion, and wherein in a third step the pouch with the implantable pulse generator is released from the insertion tool.

33. The method according to claim 31, wherein in the first step an opening of said empty pouch is at least partly shifted onto said front portion and over said front side opening, aided by using a latch on the insertion tool.

34. An insertion tool having a wall having a tubular or funnel shape, comprising, on a front portion thereof, a front side opening configured so that an opening of an empty pouch for an implantable pulse generator, and, if present, corresponding wiring, can be shifted onto said front portion and over said front side opening, and comprising, on a back portion of the insertion tool, a backside opening configured so that an implantable pulse generator can be inserted through that backside opening, through a passageway opening to the front side opening and into said pouch, while manually holding the insertion tool using said back portion,
wherein said wall comprises an axial slot between the front side opening and the backside opening
wherein the insertion tool is made of thermoplastic or thermoset material,
and/or wherein the wall is in the form of a grid or mesh.

*  *  *  *  *

18